(12) United States Patent
Fagin et al.

(10) Patent No.: US 11,331,312 B2
(45) Date of Patent: May 17, 2022

(54) TREATMENT OF H-RAS-DRIVEN TUMORS

(71) Applicant: MEMORIAL SLOAN-KETTERING CANCER CENTER, New York, NY (US)

(72) Inventors: James A. Fagin, New York, NY (US); Jeffrey A. Knauf, Wappingers Falls, NY (US); Brian R. Untch, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 15/305,778

(22) PCT Filed: Apr. 27, 2015

(86) PCT No.: PCT/US2015/027771
§ 371 (c)(1),
(2) Date: Oct. 21, 2016

(87) PCT Pub. No.: WO2015/164862
PCT Pub. Date: Oct. 29, 2015

(65) Prior Publication Data
US 2017/0042881 A1   Feb. 16, 2017

Related U.S. Application Data

(60) Provisional application No. 61/984,613, filed on Apr. 25, 2014.

(51) Int. Cl.
*A61K 31/4709* (2006.01)
*A61K 45/06* (2006.01)
*C12Q 1/6886* (2018.01)
*A61K 31/4184* (2006.01)

(52) U.S. Cl.
CPC ...... *A61K 31/4709* (2013.01); *A61K 31/4184* (2013.01); *A61K 45/06* (2013.01); *C12Q 1/6886* (2013.01); *C12Q 2600/106* (2013.01); *C12Q 2600/156* (2013.01); *G01N 2800/52* (2013.01)

(58) Field of Classification Search
CPC ............... A61K 31/4709; A61K 45/06
See application file for complete search history.

(56) References Cited

U.S. PATENT DOCUMENTS

| 2012/0283279 A1 | 11/2012 | Gilmer et al. |
| 2013/0004481 A1 | 1/2013 | Solca et al. |
| 2013/0344097 A1 | 12/2013 | Guo et al. |
| 2015/0086509 A1 | 3/2015 | Litvin et al. |

FOREIGN PATENT DOCUMENTS

| WO | WO200061145 | * | 4/2000 |
| WO | WO-2011/062930 A1 | | 5/2011 |
| WO | WO-2013/106683 A1 | | 7/2013 |
| WO | WO2013142427 | * | 9/2013 |
| WO | WO-2014/058317 A1 | | 4/2014 |

OTHER PUBLICATIONS

Prior et al. Cancer Res. (2012), vol. 72, pp. 2457-2467.*
Hong et al. J Clin Endocrinol Metab (2011), vol. 96: 997-1005.*
Liu et al. Thyroid (2008), vol. 18, pp. 853-864 (Year: 2008).*
Coehlo et al. (Arq Bras Endocrinol Metab (2007) vol. 51, pp. 612-624) (Year: 2007).*
Chen, X. et al., "Transformation by HrasG12V is Consistently Associated with Mutant Allele Copy Gains and is Reversed by Farnesyl Transferase Inhibition", Oncogene, vol. 33, pp. 5442-5449 (2014).
End, D.W., et al., "Characterization of the Antitumor Effects of the Selective Famesyl Protein Transferase Inhibitor R115777 in Vivo and in Vitro", Cancer Research, vol. 61, pp. 131-137 (2001).
Agrawal, "Farnesyltransferase inhibitor in cancer treatment," Current Cancer Treatment—Novel Beyond Conventional Approaches, InTech, pp. 149-172 (Dec. 9, 2011) ISBN 978-953-30-7397-2.
Chen et al, "Abstract 4290: The farnesyl transferase inhibitor SCH 66336 induces regression of Hras-driven tumors in mice with widespread endogenous expression of HrasG12V," Cancer Research, vol. 71, No. 8 (Apr. 2011).
Pellicano et al, "The MEK inhibitor PD184352 enhances BMS-214662-induced apoptosis in CD34 CML stem/progenitor cells," Leukemia, vol. 25, No. 7, pp. 1159-1167 (Jul. 2011).
International Search Report and Written Opinion, PCT/US2015/027771, 10 pages (dated Jul. 21, 2015).
Matallanas et al., Differences on the Inhibitory Specificities of H-Ras, K-Ras, and N-Ras (NI 7) Dominant Negative Mutants Are Related to Their Membrane Microlocalization, The Journal of Biological Chemistry, vol. 278, No. 7, Issue of Feb. 14, pp. 4572-4581, 2003.
Nassar et al., Structure of the dominant negative S17N mutant of Ras, NIH Public Access, Biochemistry. Mar. 9, 2010; 49(9): 1970-1974.
Hanrahan, E.O. et al., 'A phase II study of Lonafarnib (SCH66336) in patients with chemorefractory, advanced squamous cell carcinoma of the head and neck', American Journal of Clinical Oncology. 2009, vol. 32, No. 3, pp. 274-279.
Adjei, A.A. et al., 'Phase I Pharmacokinetic and Pharmacodynamic Study of the Oral, Small-Molecule Mitogen-Activated Protein Kinase Kinase 1/2 Inhibitor AZD6244 (ARRY-142886) in Patients With Advanced Cancers', Journal of Clinical Oncology. 2008, vol. 26, No. 13, pp. 2139-2146.
Ma, B.B.Y. et al., 'Activity of the MEK inhibitor selumetinib (AZD6244; ARRY-142886) in nasopharyngeal cancer cell lines', Investigational New Drugs. 2013, vol. 31, No. 1, pp. 30-38.

* cited by examiner

Primary Examiner — Yong S. Chong
(74) Attorney, Agent, or Firm — Foley & Lardner LLP

(57) ABSTRACT

The present disclosure describes a compositions and methods for treatment of Hras-driven cancers. Administration of a farnesyltransferase inhibitor, for example, tipifarnib, alone or in combination with a MEK inhibitor can reduce tumor size and tumor growth in cancers such as poorly differentiated thyroid cancer (PDTC) and anaplastic thyroid cancer (ATC).

5 Claims, 17 Drawing Sheets

Poorly Differentiated

Anaplastic

TREATMENT OF H-RAS-DRIVEN TUMORS

CROSS-REFERENCE TO RELATED APPLICATIONS

This application is a national phase filing under 35 U.S.C. § 371 of PCT International Application No. PCT/US2015/027771, filed on Apr. 25, 2015, which claims the benefit under 35 U.S.C. § 119(e) of U.S. Provisional Patent Application Ser. No. 61/984,613 filed Apr. 25, 2014; disclosures of the priority documents are incorporated herein by reference in their entirety.

GOVERNMENT RIGHTS STATEMENT

This invention was made with government support under grant number CA072597 awarded by the National Institutes of Health. The government has certain rights in the invention.

TECHNICAL FIELD OF THE INVENTION

The present invention generally relates to cancers associated with activating mutations of H-Ras. More particularly, the present invention relates to treatment of those cancers by administration of a farnesyltransferase inhibitor (FTI).

BACKGROUND OF THE INVENTION

RAS-driven malignancies remain a major therapeutic challenge. Hras, KrasA, KrasB and Nras are plasma membrane GTPases that exist in an active, GTP-bound or inactive, GDP-bound, state. Many human tumors have a predilection for mutations in one RAS gene family member. HRAS mutations are less common overall, but they have a particularly high prevalence in cancers of the upper aerodigestive tract, skin, thyroid and urinary bladder.

All Ras isoforms are farnesylated. Farnesyl transferase inhibitors (FTIs) block the addition of an isoprenoid group to the C-terminal portion of Ras to prevent formation of active Ras. FTIs block Hras farnesylation, membrane localization and inhibit oncogenic Hras-driven cellular transformation in vitro and in vivo. However, in most clinical trials, FTIs showed no significant antitumor activity in patients with advanced solid tumors such as lung, pancreatic and colon cancers, which mainly harbor KRAS mutations or with acute myeloid leukemia, which primarily have mutations of NRAS.

Thus, a need exists for therapeutic agents able to inhibit growth and improve outcome for patients with such cancers.

SUMMARY OF THE INVENTION

The invention provides a method for the targeted treatment of cancers associated with a constitutively activating mutation of Hras. The method comprises administering to a subject whose tumor carries a constitutively activating mutation such as Hras G12V, Hras Q61L or other constitutively activating mutation/substitution at codon 12, 13 or 61 of Hras, a therapeutically effective amount of a farnesyltransferase inhibitor (FTI).

In one aspect, therefore, the invention relates to a method for the treatment of a constitutively activating Hras mutation-driven cancer such as thyroid cancer, salivary gland cancer, head and neck squamous cell carcinoma, bladder cancer, cervical cancer using a FTI, for example, tipifarnib.

In a related aspect, the invention relates to a method for reducing tumor burden in a subject with a tumor that has a constitutively activating mutation of Hras, the method comprising administering to the subject a therapeutically effect amount of a farnesyltransferase inhibitor (FTI).

In another related aspect, the invention relates to the use of combination therapy, that is, coadministration of tipifarnib and selumitinib for the treatment of a cancer associated with a constitutively activating mutation of Hras.

In yet another related aspect, the invention relates to a method for reducing tumor burden in a subject with a tumor that has a constitutively activating mutation of Hras by exposing the tumor to a therapeutically effective amount of an FTI.

These, and other objects, features and advantages of this invention will become apparent from the following detailed description of the various aspects of the invention taken in conjunction with the accompanying drawings.

DETAILED DESCRIPTION OF THE INVENTION

Figure 1A:
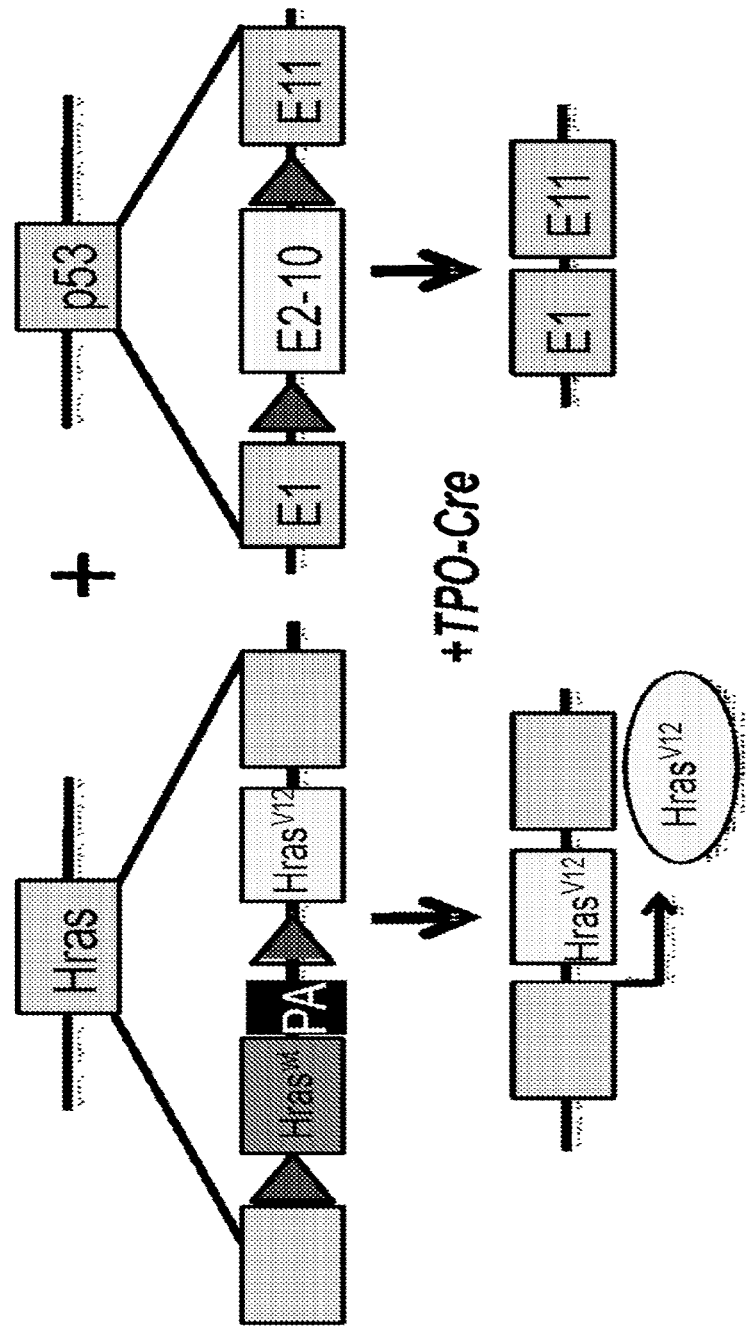
FIGS. 1A-C show that Tpo-Cre/FR-HrasG12V/p53flox/flox mice develop poorly differentiated (1C top) and anaplastic (1C bottom) thyroid cancer. (A) is a schematic showing how mutant Hras was knocked into the native mouse Hras1 gene locus in tandem with the wild-type copy (flox and replace). Upon the action of Cre recombinase, which is targeted to the thyroid with the TPO promoter, the wild-type copy is excised and replaced by HrasG12V, which is expressed physiologically under the control of the endogenous Hras gene promoter. In addition, the p53 gene is knocked out by the excision of exons 2 through 10 in the presence of Cre-recombinase. (B) is a photo of a murine tumor using the above described genetic model (homozygous for both alleles). (C) hemotoxylin and eosin (H+E) sections of tumors collected from Tpo-Cre/FR-HrasG12V/p53flox/flox mice. Tumors are either poorly differentiated (top photo) or anaplastic (bottom photo; ratio 4:1). Poorly differentiated tumors are characterized by tightly packed cuboidal shaped cells with necrosis while anaplastic tumors are well vascularized and have spindle shaped cells.
Figure 1B:
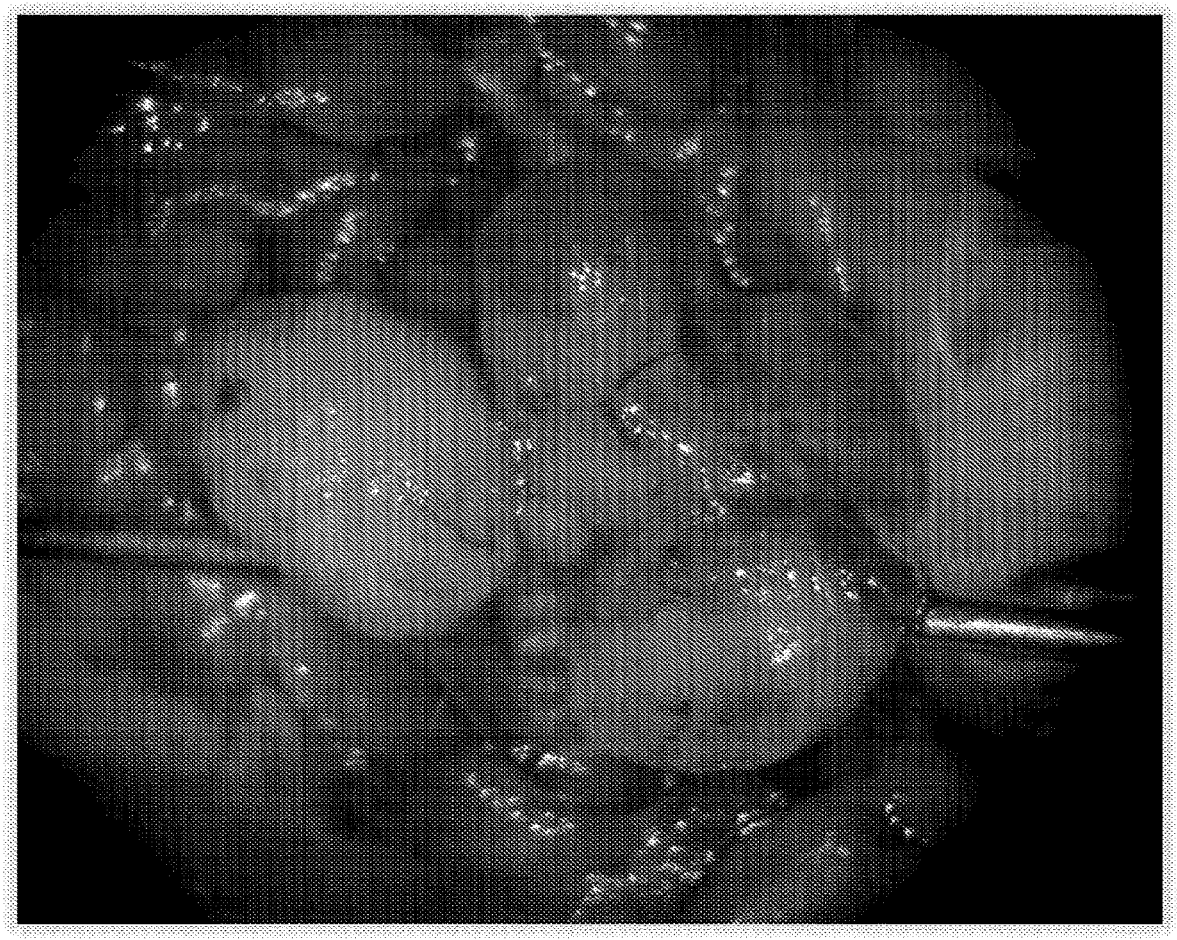

All publications, patents and other references (for example, those listed at the end of the specification) cited herein are incorporated by reference in their entirety into the present disclosure.

In accordance with the present disclosure there may be employed conventional molecular biology, microbiology, and recombinant DNA techniques within the skill of the art. Such techniques are explained in detail in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

Terms used herein are intended to be interpreted consistently with the meaning known to those of skill in the art. A few terms as they would be known in the art include the following.

As used herein, the terms "administering" and "administration" refer to any method of providing a composition disclosed herein to a subject or to bringing the composition into contact with the target tumor/cancer. Such methods are well known to those skilled in the art and include, but are not limited to, based on the location of the target tumor, oral administration, transdermal administration, administration by inhalation, nasal administration, topical administration, intravaginal administration, and parenteral administration, including injectable administration such as intravenous administration, intra-arterial administration, intramuscular administration, and subcutaneous administration. Administration can be continuous or intermittent.

The compounds may be administered alone, or in combination with one or more other compounds described herein, or in combination (i.e. co-administered) with one or more additional pharmaceutical agents. Combination therapy includes administration of a single pharmaceutical dosage formulation containing one or more of the compounds and one or more additional pharmaceutical agents, as well as administration of the compounds and each additional pharmaceutical agent, in its own separate pharmaceutical dosage formulation. For example, one or more compounds described herein and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, the compounds and one or more additional pharmaceutical agents may be administered at essentially the same time (e.g., concurrently) or at separately staggered times (e.g., sequentially).

As used herein, the term "effective amount" refers to an amount that is sufficient to achieve the desired. For example, a "effective amount" refers to an amount that is sufficient to achieve the desired therapeutic result for example, will result in inhibition in the growth of tumor/cancer cells. In some embodiments, an effective amount will result in the killing of tumor/cancer cells. The specific therapeutically effective dose level for any particular subject will depend upon a variety of factors including the severity of the disorder; the specific composition employed; the age, body weight, general health, sex and diet of the subject; the time of administration; the route of administration; the rate of excretion of the specific compound employed; the duration of the treatment; drugs and/or radiation used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days.

As used herein, the term "subject" refers to a target of administration, that is, an individual or organism, most often a patient in need of treatment for an Hras mutation-driven tumor or cancer. The subject of the herein disclosed methods can be a human or non-human mammal.

The term "tumor burden" refers to the number of cancer cells, the size of a tumor, or the amount of cancer in the body.

As used herein, the terms "treatment" or "treating" relate to any treatment of a condition associated with a presence of a mutant Hras-driven cancer, including but not limited to prophylactic treatment and therapeutic treatment. As such, the terms treatment or treating include, but are not limited to: inhibiting the progression of the condition; arresting the development of the condition; reducing the severity of the condition; ameliorating or relieving symptoms associated with the condition; and causing a regression of the condition or one or more of the symptoms associated with the condition of interest.

The presently-disclosed subject matter includes compositions and methods for targeting or producing an effect against cancer cells that harbor a constitutively activating Hras mutation, including thyroid cancer. Compositions and methods of the presently-disclosed subject matter can have utility in the treatment of thyroid cancer. Compositions of the presently-disclosed subject matter include a farnesyl transferase inhibitor (FTI), and a MEK inhibitor. In some embodiments, the compositions are pharmaceutical compositions. Methods of the presently-disclosed subject matter include administering an effective amount of a composition comprising a farnesyl transferase inhibitor (FTI) and in some embodiments, a MEK inhibitor to a subject. The presently-disclosed subject matter includes use of the compositions disclosed herein for the treatment of thyroid cancer.

The present invention is based on the observation that oncogenic Hras with p53 loss results in anaplastic and poorly differentiated thyroid tumors in a mouse model and that tipifarnib inhibits mutant Hras in these animals making tipifarnib an effective treatment for Hras-mutant cancers.

The tumor models used (anaplastic and poorly differentiated thyroid cancers) represent very aggressive malignancies with high proliferative rates. In other words, resistance to tipirfarnib that is observed in vivo in these animals is accelerated compared to what would be seen in other cancer types. In those situations where resistance following FTI targeted therapy develops, addition of a MEK inhibitor, for example, AZD6244, to a farnesyltransferase inhibitor such as tipifarnib potently inhibits the MAPK pathway and tumor growth greater than either drug alone without additional toxicity.

Many human tumors have a predilection for mutations in one RAS gene family member. However, there is no definitive explanation for the predilection for individual RAS oncogenes in different tumor lineages.

All Ras isoforms are farnesylated. Farnesyl transferase inhibitors (FTIs) block the addition of an isoprenoid group to the C-terminal portion of Ras to prevent formation of active Ras. FTIs block Hras farnesylation, membrane localization, and inhibit oncogenic Hras-driven cellular transformation in vitro (19, 20) and in vivo (21). However, in most clinical trials FTIs showed no significant antitumor activity in patients with advanced solid tumors such as lung, pancreatic and colon cancers, which mainly harbor Kras mutations (22-24), or with acute myeloid leukemia, which primarily have mutations of Nras (25). The refractoriness to FTIs of RAS-driven cancers has been attributed to compensatory geranylgeranylprenylation of Kras and Nras, which preserves their membrane targeting and function (26-28). However, the Hras selectivity of FTIs versus K- or N-ras-driven tumors has not been extensively studied in cells or in a mouse model, and no trial with an FTI had been done exclusively in patients with Hras mutant tumors.

Activating mutations of Hras are found in 4-10% of advanced metastatic thyroid cancers and in a small fraction of other malignancies, such as head and neck squamous carcinomas, salivary tumors, bladder cancer and others. The mutations occur in, for example, codons 12, 13 and 61 of HRAS. Examples of activating mutations of Hras include but are not limited to G12V and Q61L.

Growth factors and mitogens use the Ras/Raf/MEK/ERK signaling cascade to transmit signals from their receptors to regulate gene expression and prevent apoptosis. However, Ras signals through multiple effector pathways and physiological activation of the Ras/Raf/MEK/Erk pathway is influenced by multiple mechanisms, and inhibitory molecules such as MAPK phosphatases that engage the pathway at different points to negatively regulate signaling.

Determination of Tumor Hras Mutation Status

The following invention encompasses a method of treatment targeting Hras-driven tumors, specifically those tumors known to have a constitutively activating mutation of Hras.

Because treatment in accordance with this invention is targeted to such cancers, knowledge of Hras status of the tumor prior to beginning treatment can improve efficacy. In one embodiment, prior to beginning therapy, DNA or RNA from cells from the tumor are assessed to determine Hras mutation status to identify patients who are likely to benefit from FTI/MEK inhibitor therapy. Mutation status is determined using standard sequencing methods known to those skilled in the art including, for example, Sanger sequencing, next gen sequencing (NGS) etc., some of which are described in more detail in the sequencing method review publication found at the following url: iliumina.com/content/dam/illumina-marketing/documents/products/research_reviews/sequencing-methods-review.pdf.

Tumors demonstrating a constitutively activating mutation at codon 12, 13 or 61 of Hras would warrant treatment as described herein. In one embodiment, the constitutively activating mutation is G12V of Hras; in one embodiment, the constitutively activating mutation is Q61L of Hras.

Farnesyl Transferase Inhibitors

Farnesyl transferase inhibitors (FTIs) are a class of compounds that target protein farnesyltransferase with the downstream effect of preventing the proper functioning of the Ras protein. FTIs are well known in the art and some, including Tipifarnib and Lonafarnib, have been fairly well characterized with respect to toxicity, both hematological and non-hematological and pharmacokinetics.

Tipifarnib is a nonpeptidomimetic quinolinone that binds to and inhibits the enzyme, farnesyl transferase, thereby preventing the farnesylation of Ras isoforms. By inhibiting the farnesylation of these proteins, the agent prevents the activation of Ras oncogenes, inhibits cell growth, induces apoptosis and inhibits angiogenesis. Tipifarnib is commercially available from Jansen Pharmaceutica, NV under the name Zarnestra (for more details regarding tipifarnib, see U.S. Pat. Nos. 6,844,439, 6,037,350, 6,150,377, and 6,169,096; the contents of each are hereby incorporated by reference in their entirety into the present application.)

Lonafarnib is a synthetic tricyclic derivative of carboxamide that has been shown to exhibit antineoplastic properties. Like tipifarnib, lonafarnib binds to and inhibits farnesyl transferase, the enzyme involved in the post-translational modification and activation of Ras proteins. Lonafarnib is commercially available under the brand name SARASAR (Merck).

MEK Inhibitors

MEK (mitogen-activated protein kinase kinase) is a dual specificity kinase that phosphorylates both serine/threonine and tyrosine residues. MEK consists of two isoforms, MEK1 and MEK2, which in turn phosphorylate ERK1 and ERK2.

MEK inhibitors are compounds that inhibit the MAPK kinase enzymes MEK1 and/or MEK2 and therefore, can be used to affect the MAPK/ERK pathway. MEK inhibitors include but are not limited to AZD8330, Refametinib, Cobimetinib, E6201, binimetinib (MEK162), PD0325901, pimasertib, RO4987655, RO5126766, selumetinib, TAK-733, trametinib, GDC-0623, and WX-554.

Dosing

In one embodiment, tipifarnib is administered at a dose in the range of 25 to 300 mg twice a day (bid). In another embodiment, tipifarnib is administered at a dose in the range of 50 and 100 mg twice a day (bid).

In one embodiment, tipifarnib is administered orally to a subject in need thereof at a dose of 300 mg bid for 21 consecutive days of a 28 day cycle with no drug administered for the remaining 7 days of the cycle.

In another embodiment, 400 mg is administered orally bid for two consecutive weeks followed by 1 week off (no drug.)

There are alternative dosing schedules that allow for higher drug doses for shorter periods of time, for example, 600 mg po bid for 1 week followed by a break (no drug) for a week.

Dosing regimens may vary with the FTI used. One of skill in the art would be able to determine the appropriate effective dose for a particular FTI.

The dosages noted above may generally be administered for example once, twice or more per course of treatment, which may be repeated as necessary as determined by the clinician.

In one embodiment, selumenitib is co-administered (see supra) at a dose in the range of 25 to 150 mg bid; in one embodiment in the range of 50 to 100 mg bid; in one embodiment in the range of 70 to 80 mg bid.

EXAMPLES

Experimental Animals and Tipifarnib Administration.

Figure 1C:
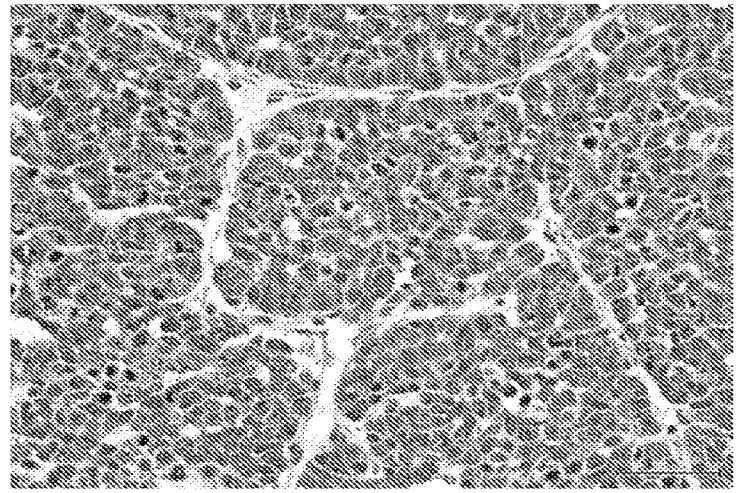
Figure 1C:
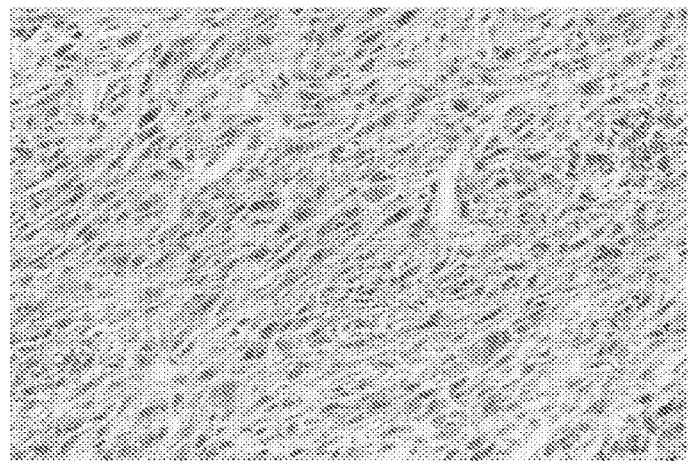
Figure 7:
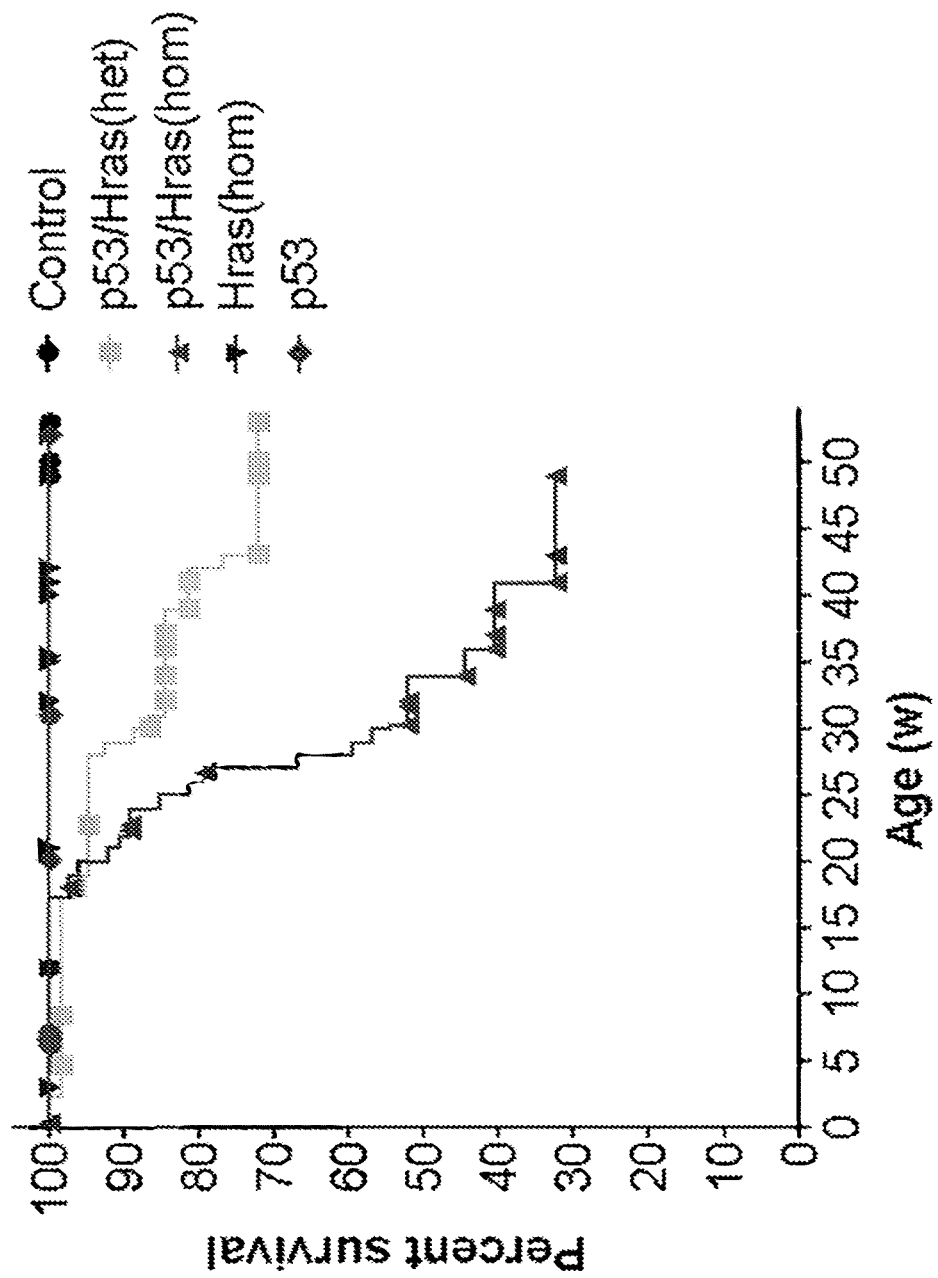
FIG. 7 is a Kaplan-Meier survival curve showing survival of TPO-Cre/Hras$^{G12V+/+}$/p53$^{flox/flox}$ mice. These mice (heterozygous-squares and homozygous-triangles) have a high mortality due to disease burden as compared to mice with control (circles) or HrasG12V (inverted triangles) or p53 (diamonds) loss alone.

Mice with thyroid-specific activation of HrasG12V and p53 loss develop aggressive thyroid tumors. Mice with thyroid-specific endogenous expression of Hras-G12V+/+ and p53 loss (TPO-Cre/Hras-G12V+/+/p53f/f) (PMID: 11694875) were generated. These mice developed highly aggressive tumors between 6 weeks and 1 year of age (FIGS. 1A, B). Immunostaining for Ki-67 and pERK was increased in these tumors, consistent with a highly proliferative tumor associated with activation of the MAP kinase pathway (data not shown). These mice have a high mortality due to disease burden as compared to mice with HrasG12V or p53 loss alone (FIG. 7). Histologic examination demonstrated that anaplastic (ATC) or poorly differentiated thyroid cancers (PDTC) occur in these mice in a ratio of approximately 1:4, respectively (FIG. 1C).

Development and characterization of mouse cell lines from TPO-Cre, Hras-G12V+/+, p53f/f mice: In order to study this model in vitro, we developed a mouse cell line (HP-ATC1) from an animal with ATC. The cell line was confirmed to harbor the HrasG12V mutation, and maintained primary tumor characteristics, including its spindle shape and the relative expression of E-cadherin and vimentin through serial passaging (x6-10).

Figure 2A:
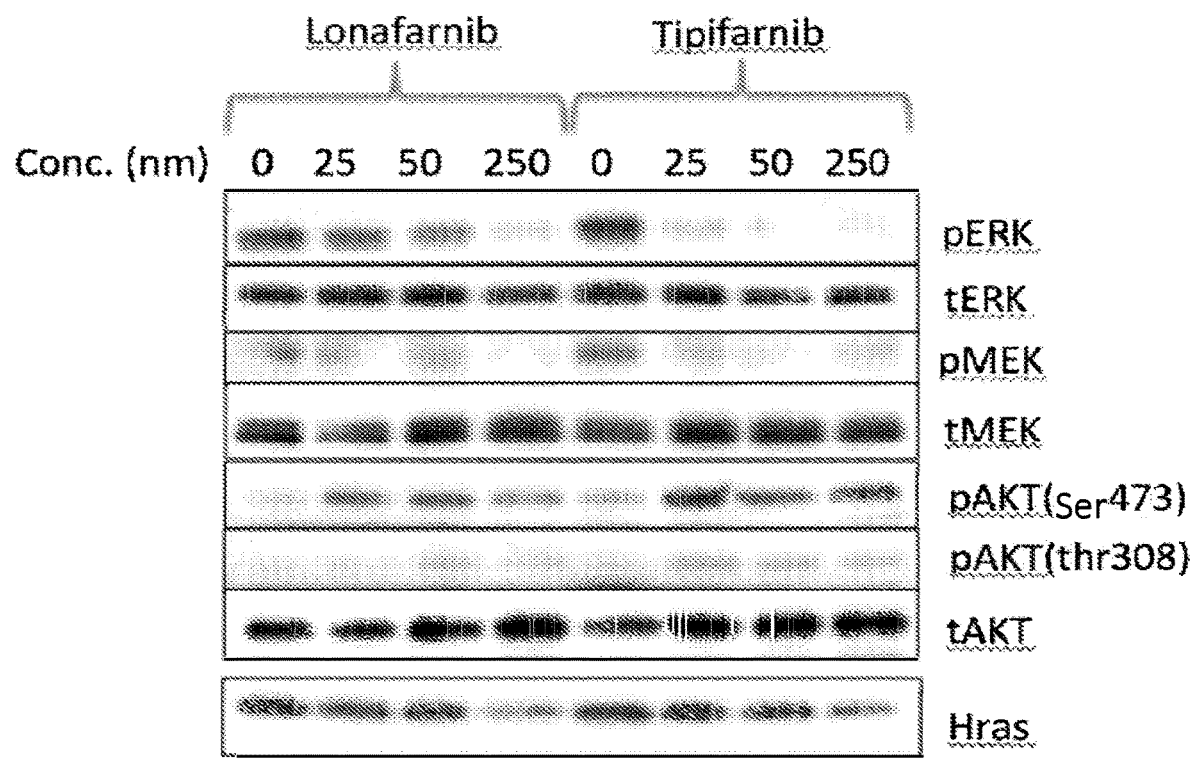
FIGS. 2A and B show the results of exposure of mouse cell lines from tumor bearing Tpo-Cre/FR-HrasG12V/p53flox/flox mice to farnesyltransferase inhibitors. Mouse cell lines were generated from tumor bearing Tpo-Cre/FR-HrasG12V/p53flox/flox mice by collagenase/dispase digestion and maintained in Coon's F-12 media with serum. After 15 passages, cells were plated in 1.5% serum and exposed to increasing concentrations of indicated drug. (A) Western blots were performed for indicated proteins (antibodies from Cell Signaling with exception of Hras which was from Santa Cruz). Tipifarnib and lonafarnib demonstrated dose dependent inhibition of the MAPK pathway signaling effectors. (B) 6 day proliferation assays from the same mouse cell line showing dose-dependent inhibition of proliferation with tipifarnib and lonafarnib.

The FTIs Tipifarnib and Lonafarnib block MAPK signaling and growth of mouse Tpo-Cre, HRas-G12V+/+, p53f/f cell line: There are currently no therapies that directly target oncogenic forms of oncogenic Ras. As farnesyl transferase inhibitors have the potential to selectively target tumors driven by mutant Hras, we treated HP-ATC1 cells with increasing concentrations of tipifarnib or lonafarnib, and found that they evoked a dose-dependent inhibition of MAPK effector phosphorylation and of proliferation (FIGS. 2A, B).

Figure 3:
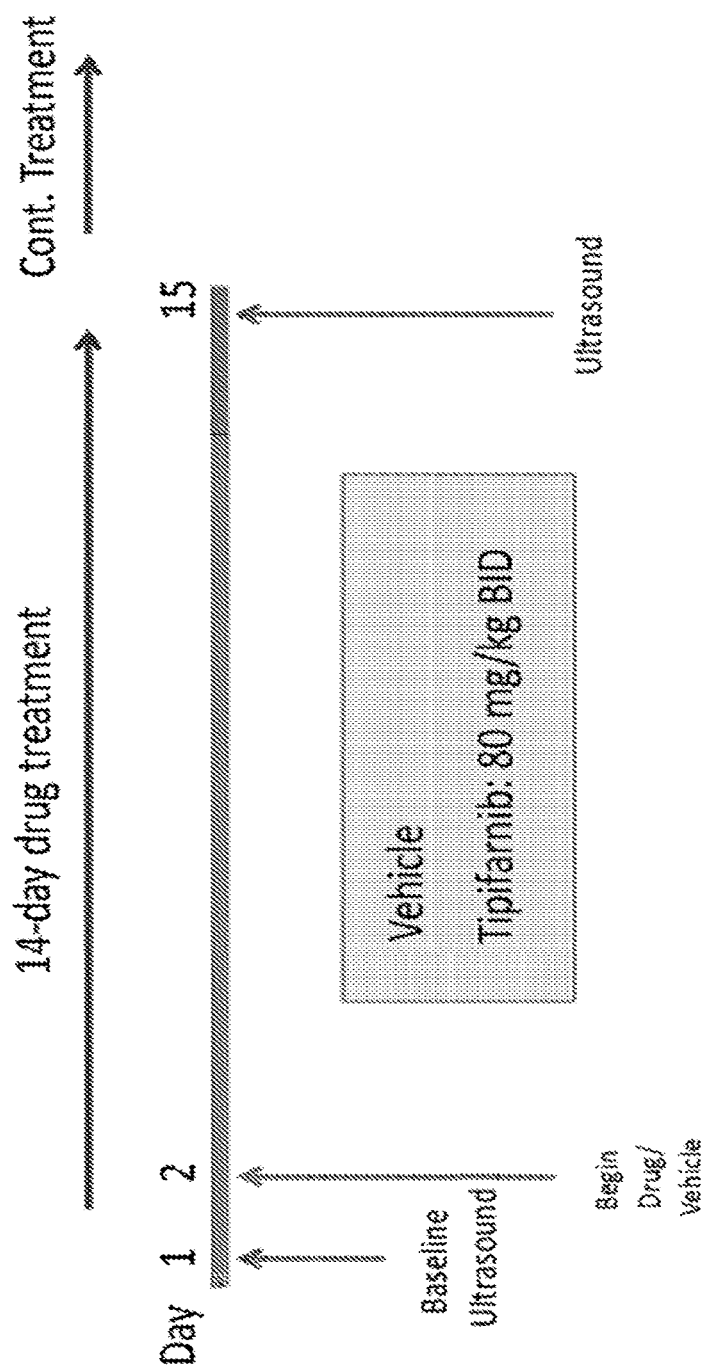
FIG. 3 is a schematic showing the design of the in vivo study of tipifarnib in Tpo-Cre/FR-Hras$^{G12V}$/p53$^{flox/flox}$ mice. Mice were treated for 14 days with tipifarnib 80 mg/kg BID by gavage. Tipifarnib was prepared in 20% beta-cyclodextran. 3D ultrasound was performed before and after treatment to assess percent change in tumor volume.
Figure 4:
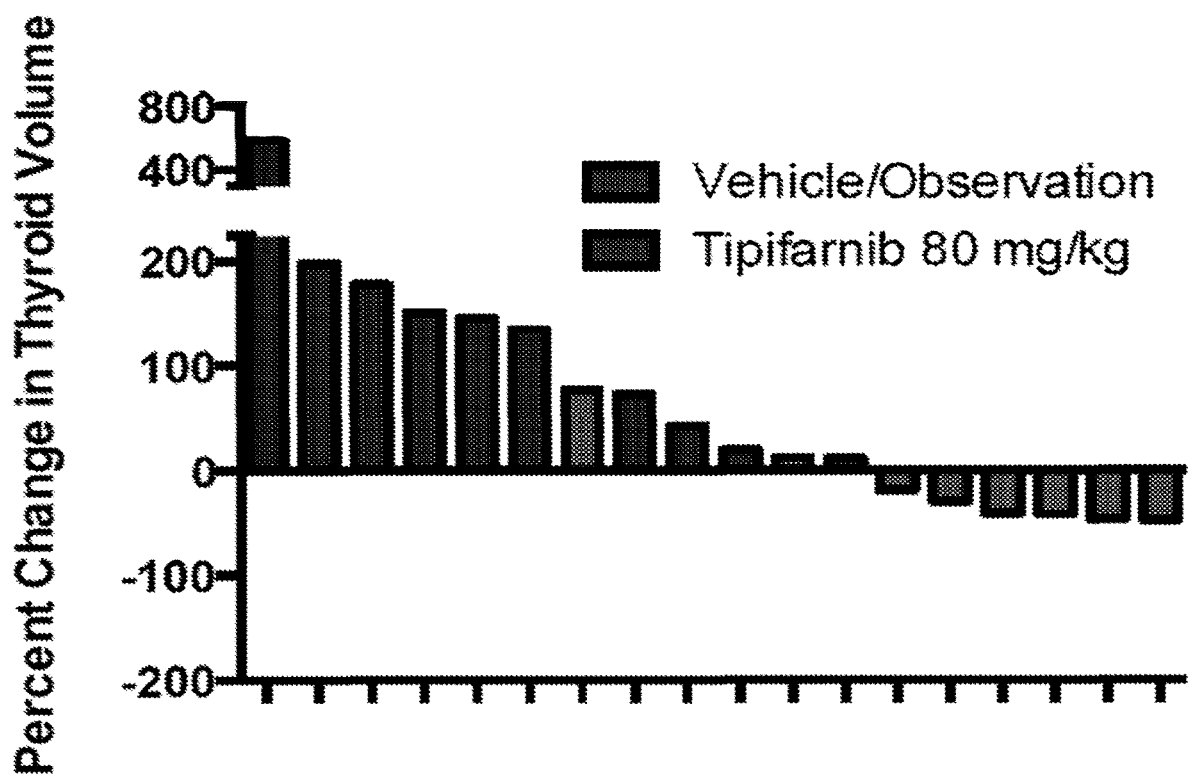
FIG. 4 is a waterfall plot demonstrating percent change in thyroid volume in mice treated with vehicle (blue) or 80 mg/kg tipifarnib BID. Tumors in each treatment group were sized matched at the beginning of therapy. Substantial reduction in growth and tumor size was seen in most cases treated with tipifarnib.
Figure 5:
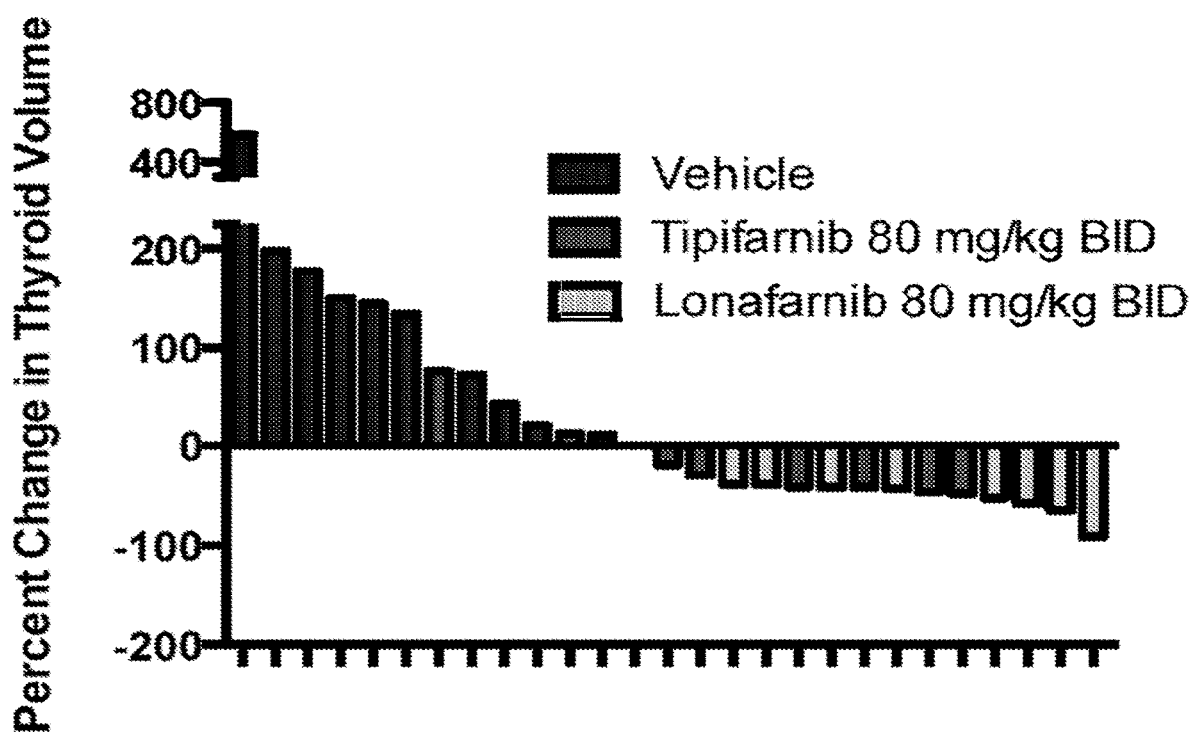
FIG. 5 is a waterfall plot of the same mice but with an additional cohort of mice treated with lonafarnib added. Of note the lonafarnib treated mice were not size matched to the vehicle group. Consistent inhibition of growth was observed between tipifarnib and lonafarnib groups.
Figure 6:
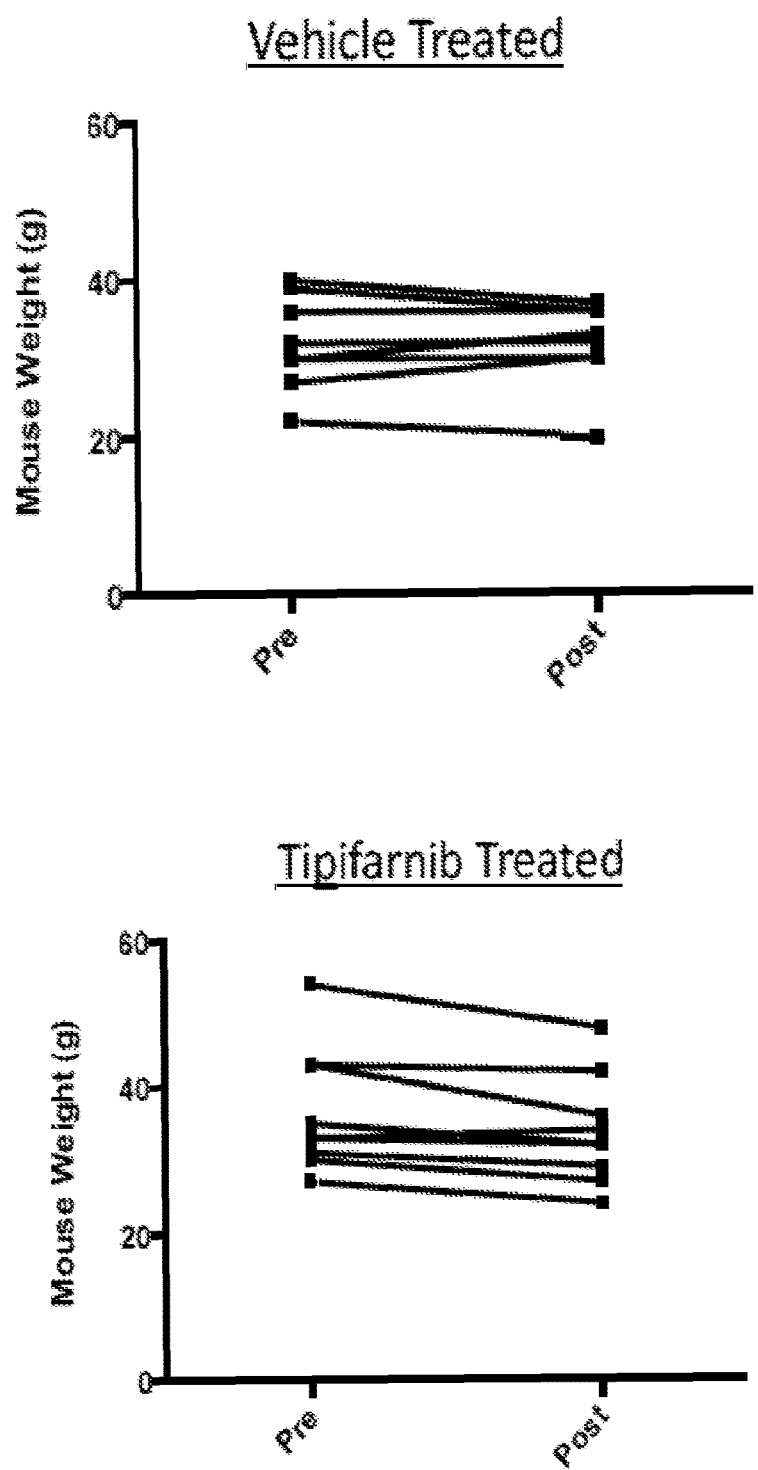
FIG. 6 shows body weight of vehicle- and tipifarnib-treated mice. No differences were seen between the two groups. Overall, minimal toxicity was observed after two weeks of treatment of tipifarnib 80 mg/kg BID.
Figure 8:
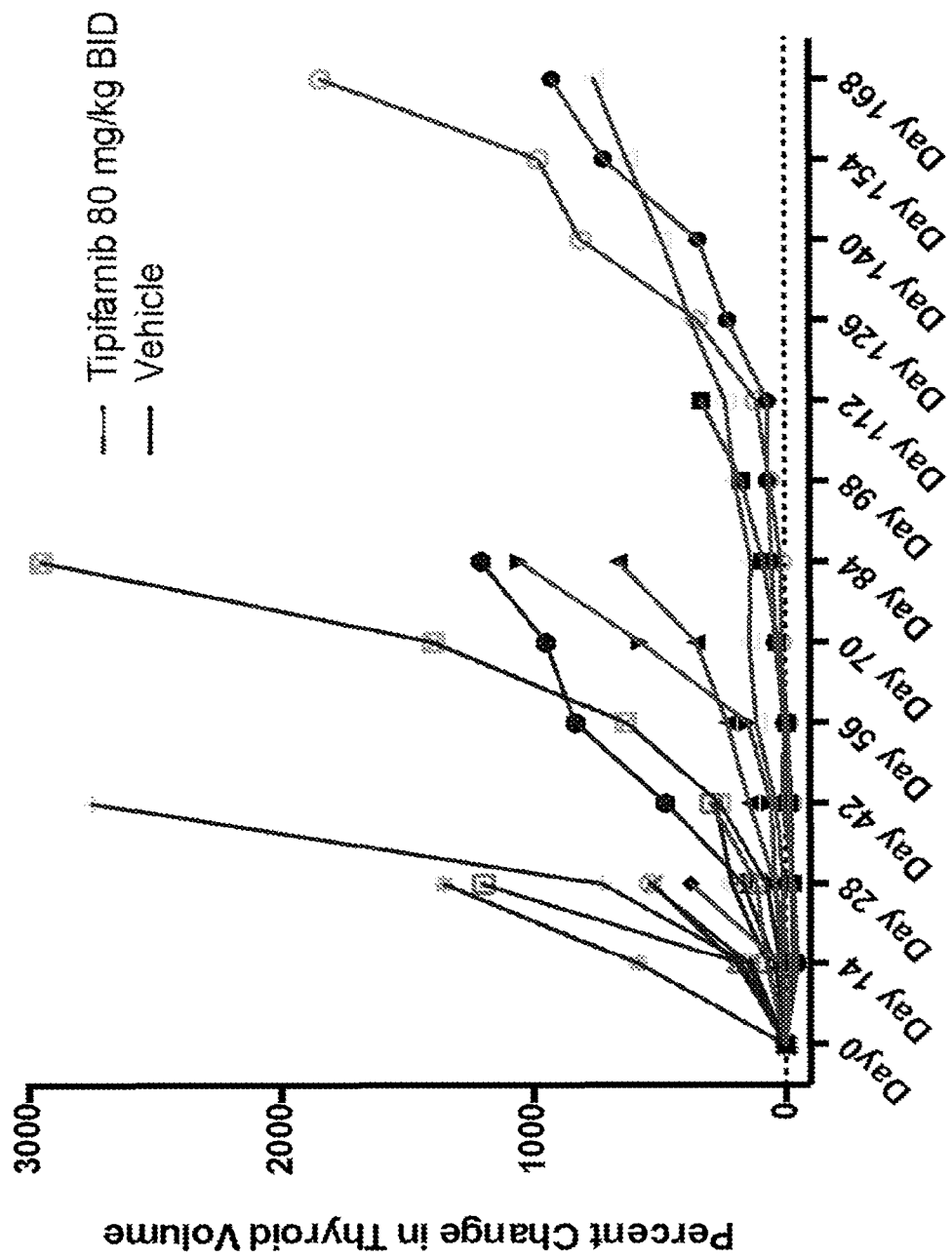
FIG. 8 shows the percent change in thyroid volume in Hras$^{G12V+/+}$/p53 null mice with thyroid cancer following treatment with vehicle or 80 mg/kg BID tipifarnib.
Figure 9:
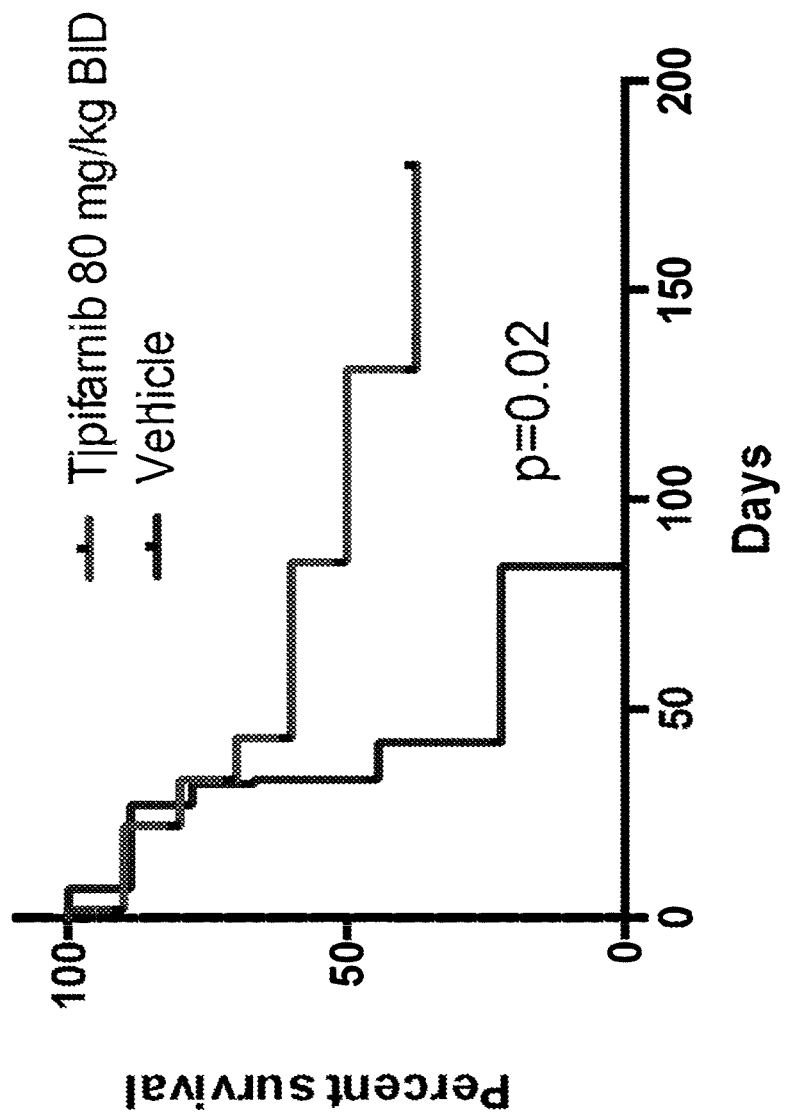
FIG. 9 is a Kaplan-Meier survival curve showing survival of TPO-Cre/Hras$^{G12v+/+}$/p53$^{flox/flox}$ mice treated with 80 mg/kg BID tipifarnib.

Treatment of mice with Hras-G12V+/+/p53-null thyroid cancers with FTIs demonstrates significant responses with resistance developing over time. The activity of these compounds in vivo was explored. Mice were treated for 2 weeks with tipifarnib or lonafarnib at 80 mg/kg twice daily (drug mixed in 20% beta-cyclodextran and given by gavage). Significant reduction in thyroid tumor volume (as measured by ultrasound) was observed compared to vehicle-treated mice (FIGS. 3,4,5). Treatment with FTIs was well tolerated in the mice with no significant differences in animal weight between vehicle and drug at 14 days (FIG. 6). Next mice were treated with Tipifarnib or vehicle for an extended time course. Of note, for this experiment tumors in each group were size-matched at the time of treatment initiation (FIG. 8). Mice treated with tipifarnib had significantly less tumor growth as compared to vehicle over the 24-week treatment period, which translated into a survival advantage (FIG. 9). However, in all tipifarnib treated animals, resistance ultimately developed as noted by increased tumor volume over time.

Figure 10:
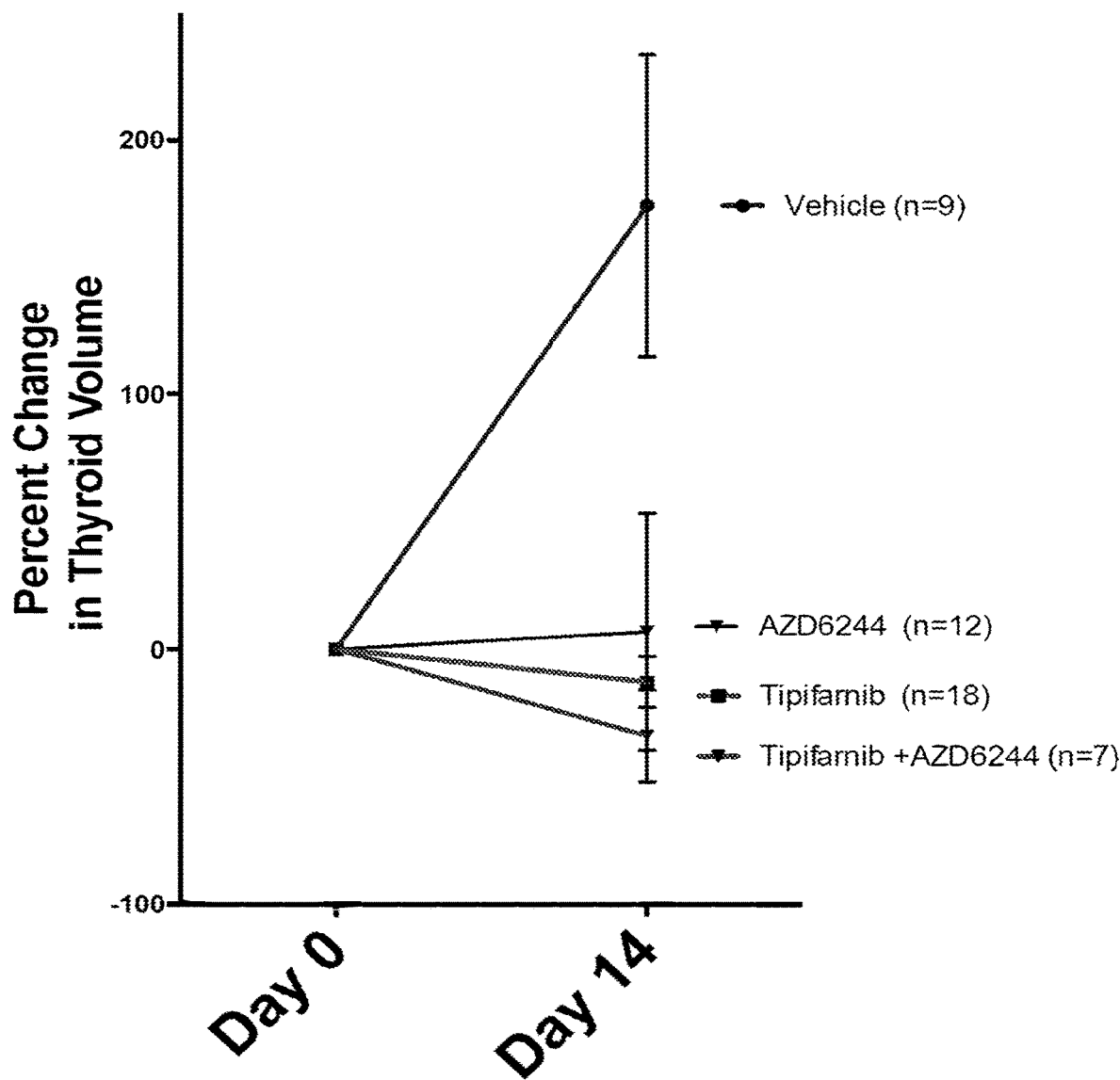
FIG. 10 shows the results of targeting resistance to tipifarnib in TPO-Cre/Hras$^{G12V+/+}$/p53$^{flox/flox}$mice by combined treatment with AZD6244. A greater reduction in tumor size was observed in the combination treatment (tipifarnib+AZD6244) for 14 days as compared to either agent alone.
Figure 11:
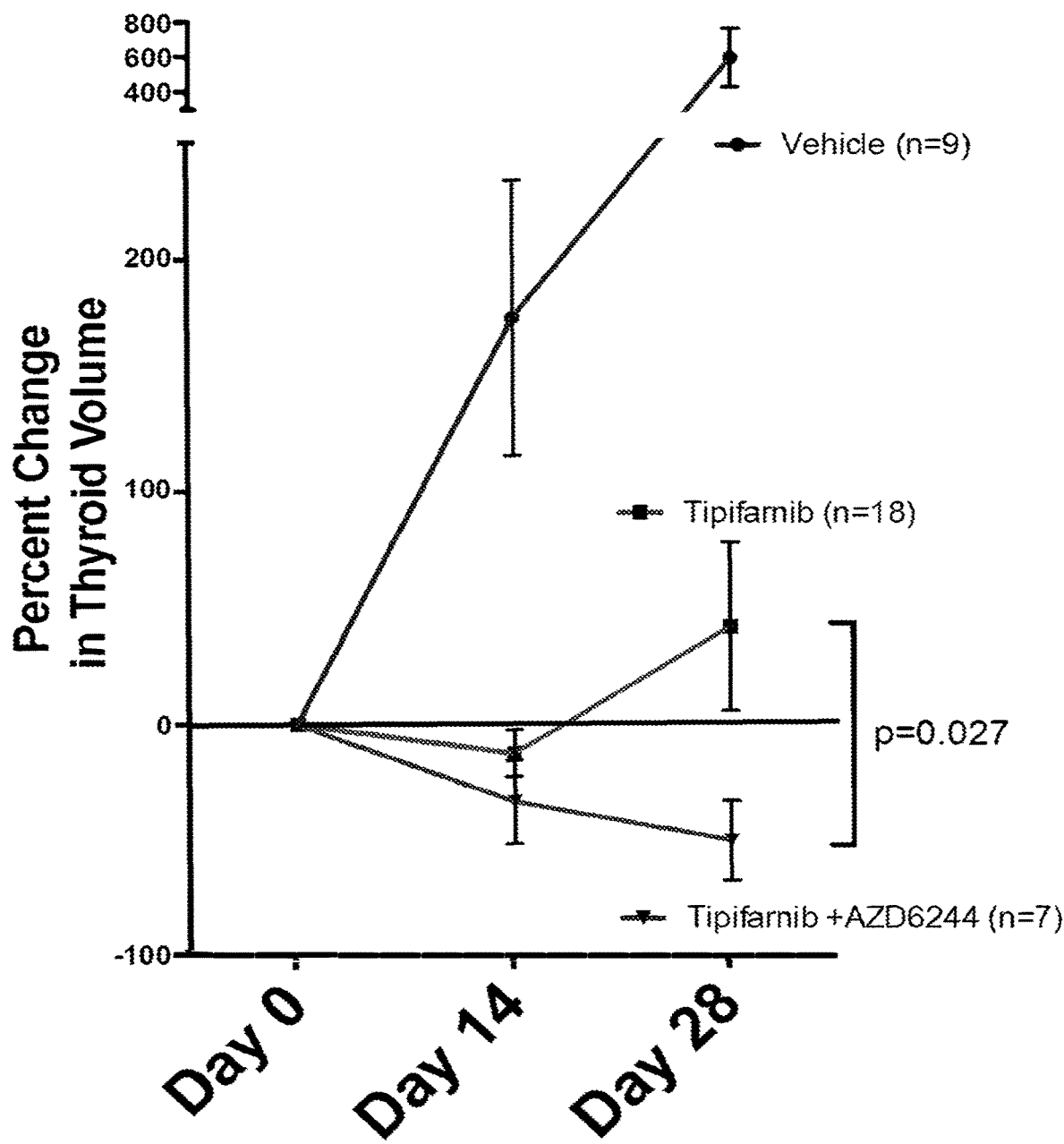
FIG. 11 shows that when treatment was extended for 28 days, increased tumor growth was seen in the tipifarnib group, whereas mice treated with the combination, tipifarnib+AZD6244, showed further reduction in tumor size.
Figure 12:
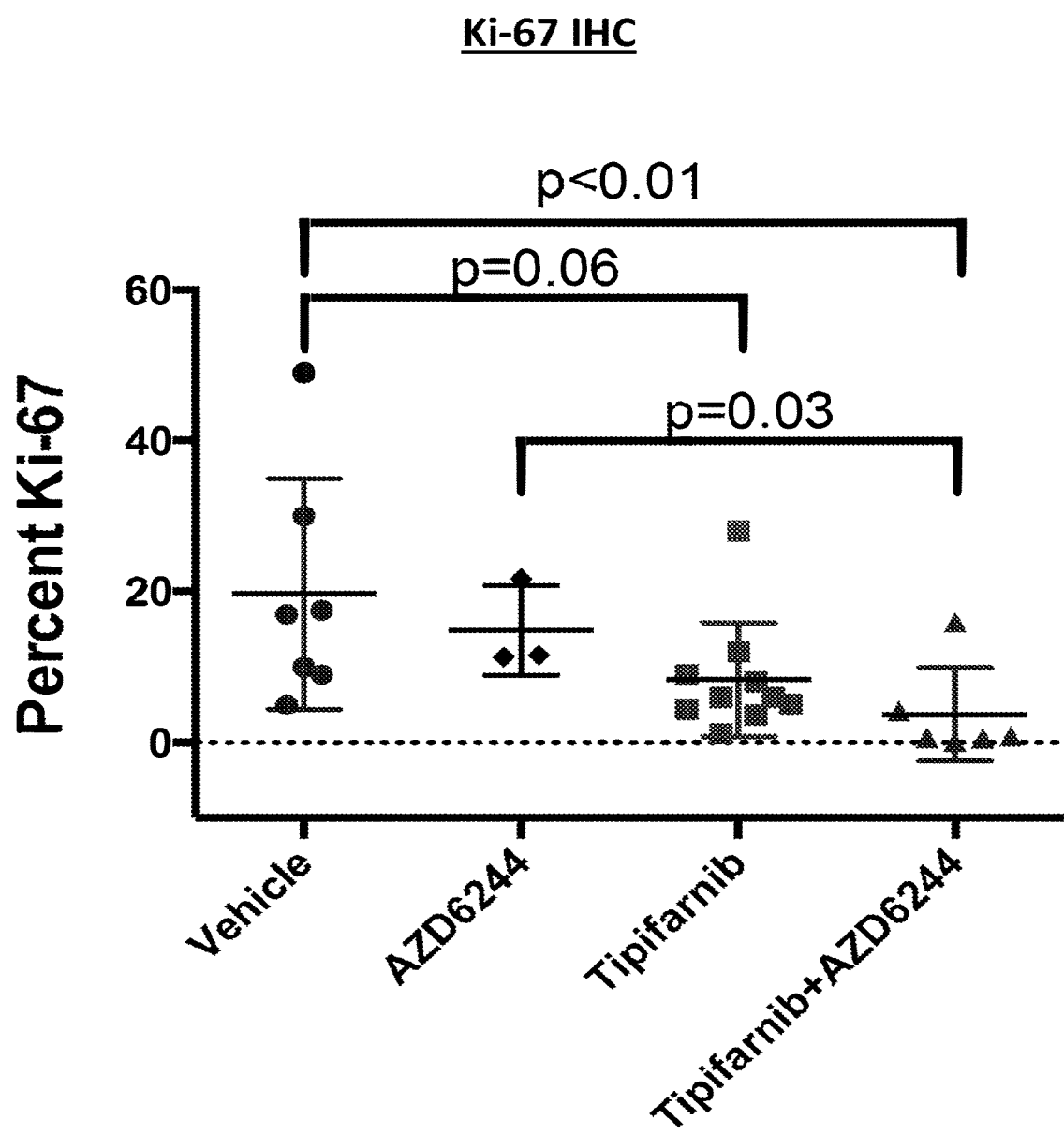
FIG. 12 shows that thyroid cancers from mice treated with the combination showed a more profound decrease in Ki-67 staining and in expression of Hmga2, a biomarker of the MAPK transcriptional output, as compared to groups receiving vehicle, AZD6244 or tipifarnib alone.
Figure 12:
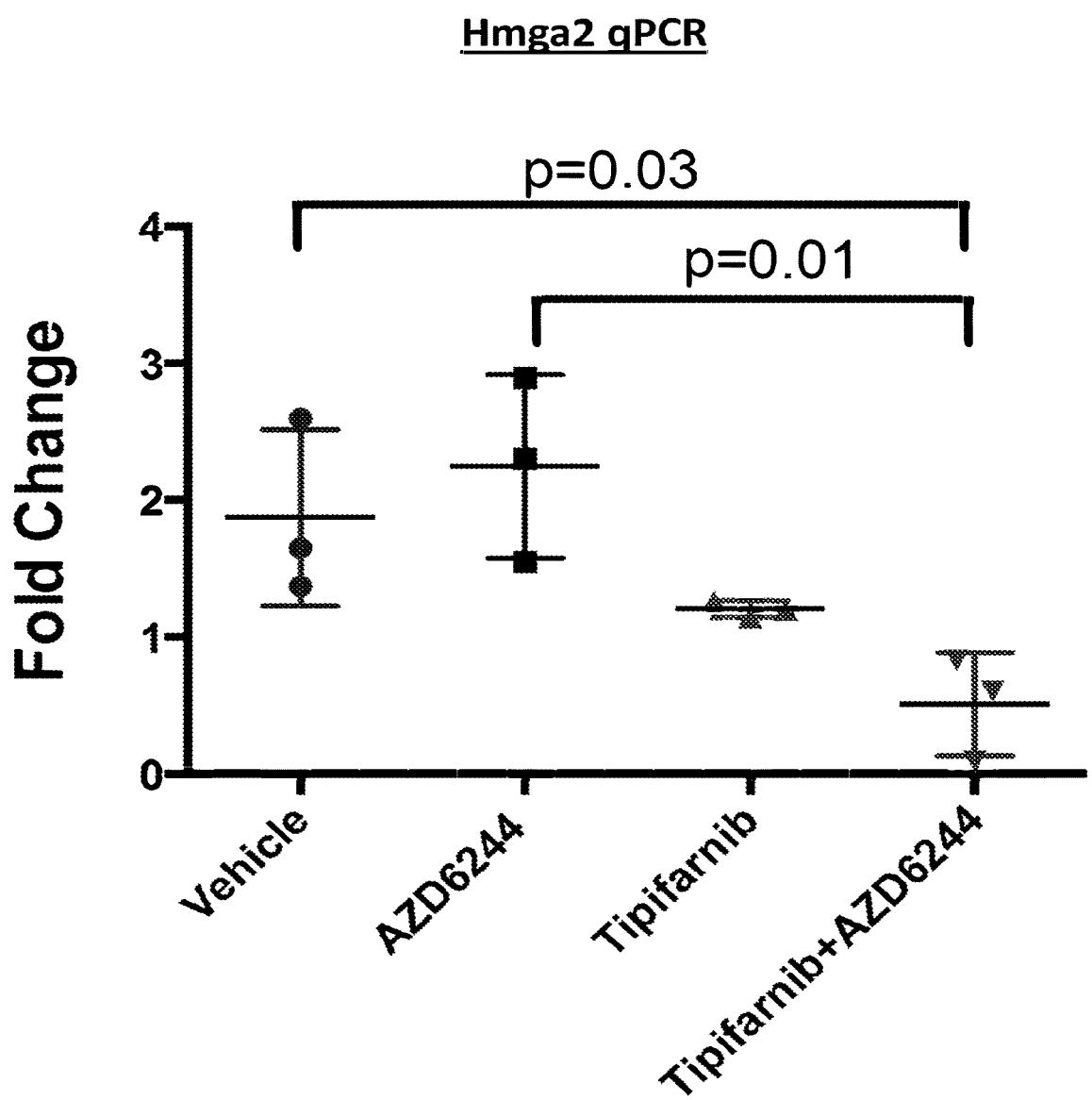

Targeting resistance to Tipifarnib in Tpo-Cre, Hras-G12V+/+, p53f/f mice by combined treatment with MEK inhibitor. Hras can signal through numerous effector pathways, including MAPK, PI3 kinase, RalGDS and others. Adaptive resistance could occur by reactivation of any of these effector pathways. Given that the MAPK pathway is central to thyroid carcinogenesis, a MEK inhibitor (AZD6244) in combination with FTI was used to prevent resistance. Mice were treated with either vehicle, 80 mg/kg tipifarnib, 25 mg/kg AZD6244 or a combination of both drugs for 14 days. Greater reduction in tumor size was observed in the combination treatment as compared to the other treatment conditions (FIG. 10). When the treatment was extended for 28 days, increased tumor growth was seen in the tipifarnib group, whereas mice treated with the combination showed further reduction in tumor size (FIG. 11). Thyroid cancers from mice treated with the combination showed a more profound decrease in Ki-67 staining and in expression of Hmga2, a biomarker of the MAPK transcriptional output, as compared to the comparator groups (FIG. 12). The combination did not demonstrate any enhanced toxicity as opposed to either drug alone.

Production of HrasG12V-p53-mice (Tpo-Cre/FR-HrasG12V/p53$^{flox/flox}$ mice). Mutant Hras was knocked into the native mouse Hras1 gene locus in tandem with the wild-type copy (flox and replace). Upon the action of Cre recombinase, which is targeted to the thyroid with the TPO promoter, the wild-type copy is excised and replaced by HrasG12V, which is expressed physiologically under the control of the endogenous Hras gene promoter. In addition, the p53 gene is knocked out by the excision of exons 2 through 10 in the presence of Cre-recombinase.

Figure 2B:
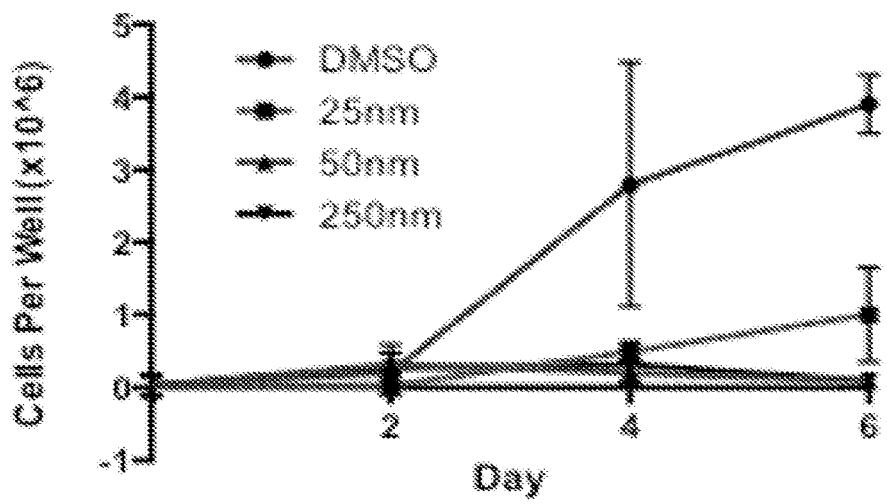
Figure 2B:
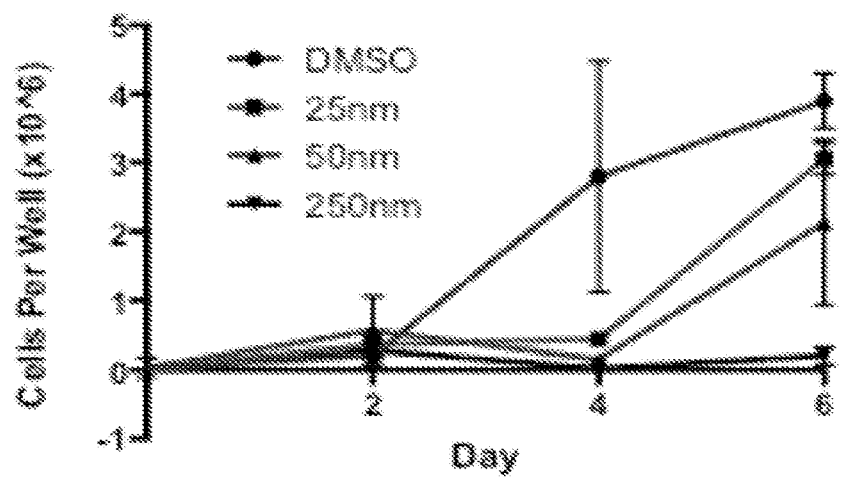
Figure 2B:
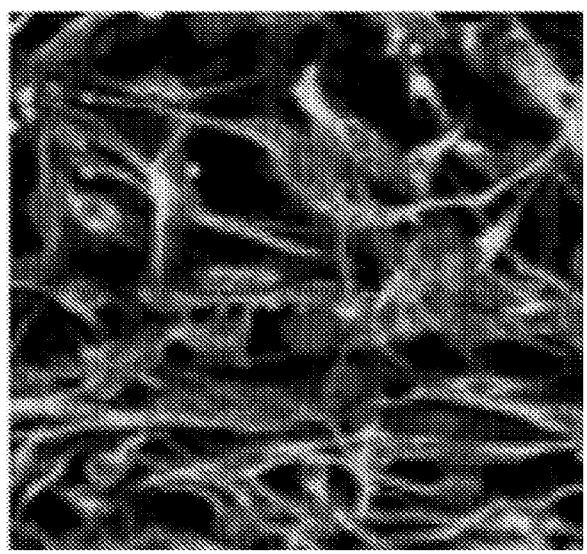

Mouse cell lines were generated from tumor bearing Tpo-Cre/FR-HrasG12V/p53flox/flox mice by collagenase/dispase digestion and maintained in Coon's F-12 media with serum. After 15 passages, cells were plated in 1.5% serum and exposed to increasing concentrations of indicated drug. Western blots were performed for indicated proteins (antibodies from Cell Signaling with exception of Hras which was from Santa Cruz). Tipifarnib and lonafarnib demonstrated dose dependent inhibitor of the MAPK pathway signaling effectors (FIG. 2A). Six (6) day proliferation assays from the same mouse cell line showed dose-dependent inhibition of proliferation with tipifarnib and lonafarnib (FIG. 2B).

Tissue Preparation, Histopathology and Immunohistochemistry.

Mice were killed by $CO_2$ asphyxiation. Normal and tumor tissue lysates were prepared for extraction of RNA, DNA or protein as described (18). Histology was performed on H&E-stained formalin-fixed paraffin embedded sections. Animal care and all procedures were approved by the MSKCC Institutional Animal Care and Use Committee.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

REFERENCES

1. Pylayeva-Gupta Y, Grabocka E, Bar-Sagi D. RAS oncogenes: weaving a tumorigenic web Nat Rev Cancer 2011; 11, 761-74.
2. Schubbert S, Shannon K, Bollag G. Hyperactive Ras in developmental disorders and cancer Nat Rev Cancer 2007; 7, 295-308.
3. Karnoub A E, Weinberg R A. Ras oncogenes: split personalities Nat Rev Mol Cell Biol 2008; 9, 517-31.
4. Castellano E, Santos E. Functional specificity of ras isoforms: so similar but so different Genes Cancer 2011; 2, 216-31.
5. Leon J, Guerrero I, Pellicer A. Differential expression of the ras gene family in mice Mol Cell Biol 1987; 7, 1535-40.
6. Ahearn I M, Haigis K, Bar-Sagi D, Philips M R. Regulating the regulator: post-translational modification of RAS Nat Rev Mol Cell Biol 2011; 13, 39-51.
7. Apolloni A, Prior I A, Lindsay M, Parton R G, Hancock J F. H-ras but not K-ras traffics to the plasma membrane through the exocytic pathway Mol Cell Biol 2000; 20, 2475-87.
8. Esteban L M, Vicario-Abejon C, Fernandez-Salguero P, Fernandez-Medarde A, Swaminathan N, Yienger K, et al. Targeted genomic disruption of H-ras and N-ras, individually or in combination, reveals the dispensability of both loci for mouse growth and development Mol Cell Biol 2001; 21, 1444-52.
9. Plowman S J, Williamson D J, O'Sullivan M J, Doig J, Ritchie A M, Harrison D J, et al. While K-ras is essential for mouse development, expression of the K-ras 4A splice variant is dispensable Mol Cell Biol 2003; 23, 9245-50.
10. Johnson L, Greenbaum D, Cichowski K, Mercer K, Murphy E, Schmitt E, et al. K-ras is an essential gene in the mouse with partial functional overlap with N-ras Genes Dev 1997; 11, 2468-81.
11. Quintanilla M, Brown K, Ramsden M, Balmain A. Carcinogen-specific mutation and amplification of Ha-ras during mouse skin carcinogenesis Nature 1986; 322, 78-80.
12. Balmain A, Ramsden M, Bowden G T, Smith J. Activation of the mouse cellular Harvey-ras gene in chemically induced benign skin papillomas Nature 1984; 307, 658-60.
13. Ise K, Nakamura K, Nakao K, Shimizu S, Harada H, Ichise T, et al. Targeted deletion of the H-ras gene decreases tumor formation in mouse skin carcinogenesis Oncogene 2000; 19, 2951-6.
14. To M D, Rosario R D, Westcott P M, Banta KL, Balmain A. Interactions between wild-type and mutant Ras genes in lung and skin carcinogenesis Oncogene 2012; 10.
15. Bremner R, Balmain A. Genetic changes in skin tumor progression: correlation between presence of a mutant ras gene and loss of heterozygosity on mouse chromosome 7 Cell 1990; 61, 407-17.
16. Buchmann A, Ruggeri B, Klein-Szanto A J, Balmain A. Progression of squamous carcinoma cells to spindle carcinomas of mouse skin is associated with an imbalance of H-ras alleles on chromosome 7 Cancer Res 1991; 51, 4097-101.
17. Schuhmacher A J, Guerra C, Sauzeau V, Canamero M, Bustelo X R, Barbacid M. A mouse model for Costello syndrome reveals an Ang II-mediated hypertensive condition J Clin Invest 2008; 118, 2169-79.
18. Chen X, Mitsutake N, LaPerle K, Akeno N, Zanzonico P, Longo V A, et al. Endogenous expression of Hras(G12V) induces developmental defects and neoplasms with copy number imbalances of the oncogene Proc Natl Acad Sci U SA 2009; 106, 7979-84.
19. Bishop W R, Bond R, Petrin J, Wang L, Patton R, Doll R, et al. Novel tricyclic inhibitors of farnesyl protein transferase. Biochemical characterization and inhibition of Ras modification in transfected Cos cells J Biol Chem 1995; 270, 30611-8.
20. Kohl N E, Mosser S D, deSolms S J, Giuliani E A, Pompliano D L, Graham S L, et al. Selective inhibition of ras-dependent transformation by a farnesyltransferase inhibitor Science 1993; 260, 1934-7.
21. Kohl N E, Omer C A, Conner M W, Anthony N J, Davide J P, deSolms S J, et al. Inhibition of farnesyltransferase induces regression of mammary and salivary carcinomas in ras transgenic mice Nat Med 1995; 1, 792-7.
22. Van C E, van d, V, Karasek P, Oettle H, Vervenne W L, Szawlowski A, et al. Phase III trial of gemcitabine plus tipifarnib compared with gemcitabine plus placebo in advanced pancreatic cancer J Clin Oncol 2004; 22, 1430-8.
23. Rao S, Cunningham D, de G A, Scheithauer W, Smakal M, Humblet Y, et al. Phase III double-blind placebo-controlled study of farnesyl transferase inhibitor R115777 in patients with refractory advanced colorectal cancer J Clin Oncol 2004; 22, 3950-7.
24. Johnson B E, Heymach J V. Farnesyl transferase inhibitors for patients with lung cancer Clin Cancer Res 2004; 10, 4254s-7s.
25. Harousseau J L, Martinelli G, Jedrzejczak W W, Brandwein J M, Bordessoule D, Masszi T, et al. A randomized phase 3 study of tipifarnib compared with best supportive care, including hydroxyurea, in the treatment of newly diagnosed acute myeloid leukemia in patients 70 years or older Blood 2009; 114, 1166-73.
26. Casey P J, Solski P A, Der C J, Buss J E. p21ras is modified by a farnesyl isoprenoid Proc Natl Acad Sci USA 1989; 86, 8323-7.
27. Zhang F L, Kirschmeier P, Carr D, James L, Bond R W, Wang L, et al. Characterization of Ha-ras, N-ras, Ki-Ras4A, and Ki-Ras4B as in vitro substrates for farnesyl protein transferase and geranylgeranyl protein transferase type I J Biol Chem 1997; 272, 10232-9.
28. Whyte D B, Kirschmeier P, Hockenberry T N, Nunez-Oliva I, James L, Catino J J, et al. K- and N-Ras are geranylgeranylated in cells treated with farnesyl protein transferase inhibitors J Biol Chem 1997; 272, 14459-64.
29. Bastian B C, LeBoit P E, Pinkel D. Mutations and copy number increase of HRAS in Spitz nevi with distinctive histopathological features Am J Pathol 2000; 157, 967-72.

30. Namba H, Gutman R A, Matsuo K, Alvarez A, Fagin J A. H-ras protooncogene mutations in human thyroid neoplasms J Clin Endocrinol Metab 1990; 71, 223-9.
31. Takano T, Ohe Y, Sakamoto H, Tsuta K, Matsuno Y, Tateishi U, et al. Epidermal growth factor receptor gene mutations and increased copy numbers predict gefitinib sensitivity in patients with recurrent non-small-cell lung cancer J Clin Oncol 2005; 23, 6829-37.
32. Modrek B, Ge L, Pandita A, Lin E, Mohan S, Yue P, et al. Oncogenic activating mutations are associated with local copy gain Mol Cancer Res 2009; 7, 1244-52.
33. Hayes T K, Der C J. Mutant and wild-type Ras: co-conspirators in cancer Cancer Discov 2013; 3, 24-6.
34. Zhang Z, Wang Y, Vikis H G, Johnson L, Liu G, Li J, et al. Wildtype Kras2 can inhibit lung carcinogenesis in mice Nat Genet 2001; 29, 25-33.
35. Diaz R, Lue J, Mathews J, Yoon A, Ahn D, Garcia-Espana A, et al. Inhibition of Ras oncogenic activity by Ras protooncogenes Int J Cancer 2005; 113, 241-8.
36. Diaz R, Ahn D, Lopez-Barcons L, Malumbres M, Perez D C, I, Lue J, et al. The N-ras proto-oncogene can suppress the malignant phenotype in the presence or absence of its oncogene Cancer Res 2002; 62, 4514-8.
37. Finney R E, Bishop J M. Predisposition to neoplastic transformation caused by gene replacement of H-ras1 Science 1993; 260, 1524-7.
38. Lim K H, Ancrile B B, Kashatus D F, Counter C M. Tumour maintenance is mediated by eNOS Nature 2008; 452, 646-9.
39. Young A, Lou D, McCormick F. Oncogenic and wild-type Ras play divergent roles in the regulation of mitogen-activated protein kinase signaling Cancer Discov 2013; 3, 112-23.
40. Jeng H H, Taylor L J, Bar-Sagi D. Sos-mediated cross-activation of wild-type Ras by oncogenic Ras is essential for tumorigenesis Nat Commun 2012; 3:1168. doi: 10.1038/ncomms2173, 1168.
41. Gordon L B, Kleinman M E, Miller D T, Neuberg D S, Giobbie-Hurder A, Gerhard-Herman M, et al. Clinical trial of a farnesyltransferase inhibitor in children with Hutchinson-Gilford progeria syndrome Proc Natl Acad Sci USA 2012; 109, 16666-71.
42. Boichard A, Croux L, Al G A, Broutin S, Dupuy C, Lebouleux S, et al. Somatic RAS mutations occur in a large proportion of sporadic RET-negative medullary thyroid carcinomas and extend to a previously unidentified exon J Clin Endocrinol Metab 2012; 97, E2031-E2035.
43. Moura M M, Cavaco B M, Pinto A E, Leite V. High prevalence of RAS mutations in RET-negative sporadic medullary thyroid carcinomas J Clin Endocrinol Metab 2011; 96, E863-E868.
44. Chen X, Makarewicz J M, Knauf J A, Fagin J A. Transformation by Hras$^{G12V}$ is consistently associated with mutant allele copy gains and is reversed by farnesyl transferase inhibition. Oncogene 2013; 1-8.

We claim:

1. A method for treating a patient with a thyroid cancer having a constitutively activating mutation of Hras, comprising administering to the patient a therapeutically effective amount of farnesyltransferase inhibitor (FTI) monotherapy,
wherein administration of the therapeutically effective amount of FTI monotherapy reduces thyroid tumor volume in the patient compared to an untreated control subject suffering from the thyroid cancer,
wherein the FTI is tipifarnib or lonafarnib, and
wherein the constitutively activating mutation comprises a substitution at codon 12, 13 or 61, of Hras.

2. The method of claim 1, further comprising detecting the constitutively activating mutation of Hras in a DNA or RNA sample from a cancer cell from the patient prior to administering the FTI.

3. The method of claim 1, wherein the constitutively activating mutation is G12V of Hras.

4. The method of claim 1, wherein the constitutively activating mutation is Q61L of Hras.

5. A method for prolonging survival of a patient with a thyroid cancer having a constitutively activating mutation of Hras, comprising administering to the patient a therapeutically effective amount of farnesyltransferase inhibitor (FTI) monotherapy,
wherein administration of the therapeutically effective amount of FTI monotherapy prolongs survival of the patient compared to an untreated control subject suffering from the thyroid cancer,
wherein the FTI is tipifarnib or lonafarnib, and
wherein the constitutively activating mutation comprises a substitution at codon 12, 13 or 61, of Hras.

* * * * *